United States Patent [19]

Daniell et al.

[11] E Patent Number: Re. 33,219

[45] Reissued Date of Patent: May 22, 1990

[54] CLAMP VALVES

[75] Inventors: Michael G. Daniell; Gerald S. Martin, both of Auckland, New Zealand

[73] Assignee: Fisher & Paykel Limited, Auckland, New Zealand

[21] Appl. No.: 293,198

[22] Filed: Jan. 4, 1989

Related U.S. Patent Documents

Reissue of:

[64] Patent No.: 4,634,092
Issued: Jan. 6, 1987
Appl. No.: 656,724
Filed: Oct. 1, 1984

[30] Foreign Application Priority Data

Sep. 30, 1984 [NZ] New Zealand ..... 205826

[51] Int. Cl.[5] ..... F16L 55/14

[52] U.S. Cl. ..... 251/7; 251/90; 604/250

[58] Field of Search ..... 251/4, 5, 7, 8, 90, 251/321, 337; 604/250

[56] References Cited

U.S. PATENT DOCUMENTS

| | | | |
|---|---|---|---|
| 3,213,882 | 10/1965 | Beatty . | |
| 3,264,067 | 8/1966 | Alderfer | 251/7 |
| 3,450,148 | 6/1969 | Mongelluzzo et al. | 137/382 |
| 3,998,364 | 12/1976 | Hollander . | |
| 4,230,151 | 10/1980 | Jonsson | 251/7 |

*Primary Examiner*—John Fox

*Attorney, Agent, or Firm*—Fleit, Jacobson, Cohn, Price, Holman & Stern

[57] ABSTRACT

A clamp valve is made which comprises a hollow member open at one end and which has a pair of apertures through side walls thereof. A slide is movable in the hollow member and has a transverse aperture therethrough so that a conduit which has a pliable resilient wall can in use be passed through both of the apertures in the hollow member and the aperture in the slide. Biassing means are provided to bias the slide relative to the hollow member so that the conduit is in use normally clamped between an edge of the aperture in the slide and an edge of one of the apertures in the hollow member so that the conduit is normally closed to fluid flow.

5 Claims, 2 Drawing Sheets

CLAMP VALVES

Matter enclosed in heavy brackets [ ] appears in the original patent but forms no part of this reissue specification; matter printed in italics indicates the additions made by reissue.

This invention relates to a clamp valves.

In many applications, a squeeze clamp is used for controlling the flow of fluids through a tube. In some applications, especially medical, it is essential that the fluid only flows when the operator is in attendance and operating the valve. One available clamp which serves this function, uses a stainless steel leaf spring as a functional member, which although effective in use is costly in production which is clearly disadvantgeous.

It is an object of the present invention to provide a clamp valve which will go at least some distance towards meeting the foregoing desiderata or which will at least provide the public with a useful choice.

Accordingly the invention consists in a clamp valve comprising a hollow member open at one end and having a pair of apertures through the side walls thereof, a slide movable in said hollow member and having a transverse aperture therethrough so that a conduit having a pliable resilient wall can in use be passed through both said apertures in said hollow member and said aperture in said slide, and biasing means to bias said slide relative to said hollow member so that said conduit is in use normally clamped between an edge of said aperture in said slide and an edge of at least one said aperture in said hollow member so that said conduit is normally closed to fluid flow.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

One preferred form of the invention will now be described with reference to the accompanying drawings in which.

Figure 1:
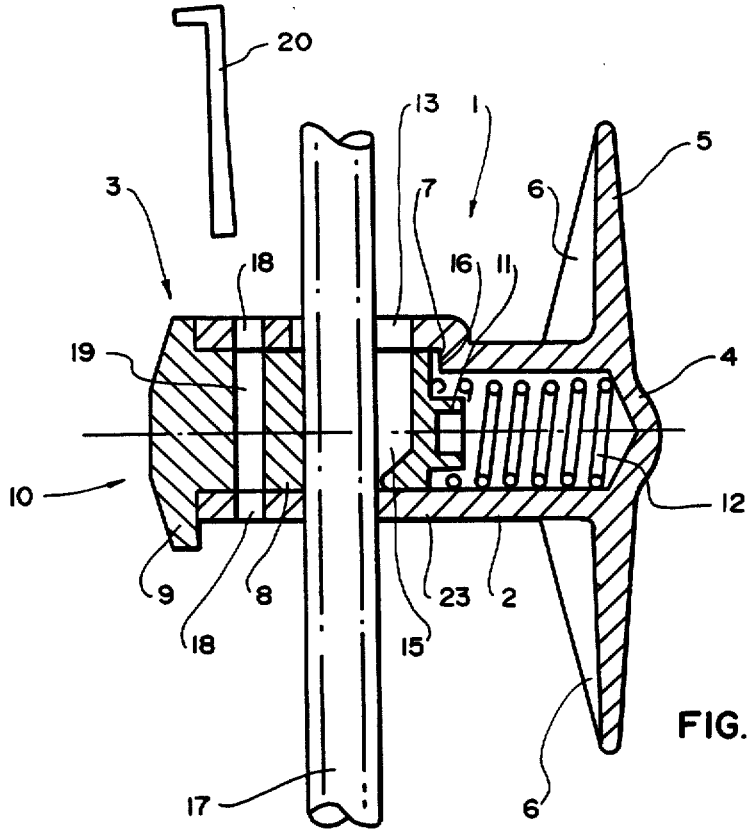
FIG. 1 is a diagrammatic cross sectional view of a clamp valve according to the preferred form of the invention with the valve in the open position.

Referring to the drawings a clamp valve 1 is provided which comprises a hollow member 2 open at end 3 and substantially closed, preferably completely closed, at the other end 4.

The hollow member 2 preferably provides near end 4 or at end 4 as shown in the drawings a plate 5 which may be strengthened by buttresses 6 between the plate 5 and the body of the hollow member 2. The plate 5 extends outwardly of the hollow member 2 and provides a hand or finger grip in use.

The hollow member 2 also preferably includes an inwardly extending step at 7 which may be circumferential or be provided around only part of the circumference as shown in the drawings.

Within the hollow member 2 is provided a slide 8 which moves in the hollow member 2 between the end 3 and the step 7. The slide 8 preferably has an enlarged head or button 9 at its outward end 10 and preferably also further includes a spigot 11 at its inner end so that a biasing means preferably a compression spring 12 may be positioned between the slide 8 and the end 4 of the hollow member 2, the spigot 11 forming a location member for the spring 12.

Figure 2:
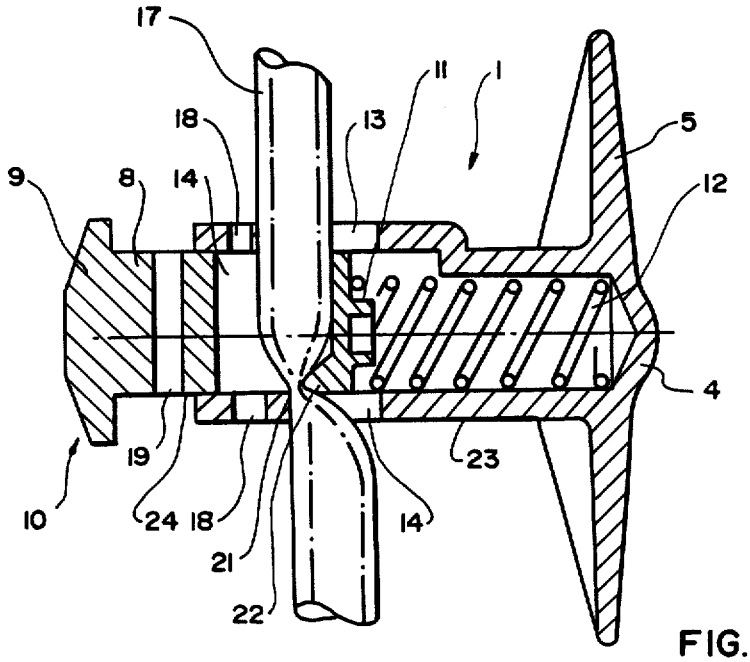
FIG. 2 is a cross sectional view of a clamp valve according to the invention in a substantially closed position.
Figure 3:
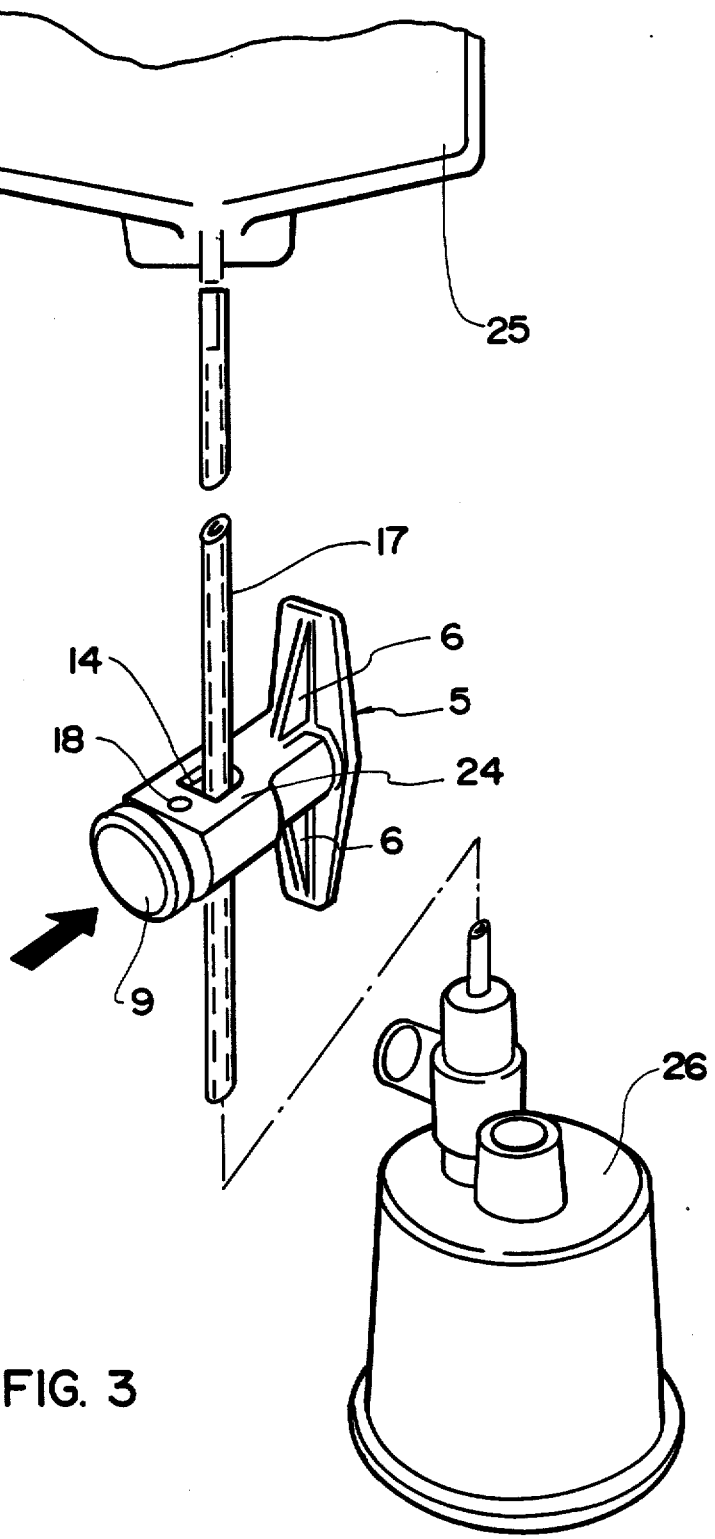
FIG. 3 is a perspective view illustrating one particular use of the clamp valve of the invention the clamp being upside down with respect to FIGS. 1 and 2.

The hollow member 2 has a pair of apertures therein preferably oppositely spaced comprising a first aperture 13 and a second aperture 14. The slide 8 also has an aperture 15 therethrough and the apertures 13, 14 and 15 are desirably aligned so that with the inward end 16 of the slide adjacent the step 7 the apertures 13, 14 and 15 are substantially in alignment so that in use a conduit 17 can be passed therethrough for example as shown in FIGS. 1 and 2. In the construction illustrated the aperture 13 is longer (in the direction of the longitudinal axis of the clamp 1) than the apertures 14 and 15 and aperture 15 is wider than aperture 14. Aperture 15 is desirably of size little greater than the diameter of the conduit 17 which it is desired to clamp.

Means are provided to retain the clamp substantially in this position and this may comprise a pair of further apertures 18 in the hollow member 2 as well as a further aperture 19 in the slide 8 which can be aligned (with the clamp substantially in the open position) so that a pin 20 or the like can be passed through the aligned apertures 18 and 19.

In order for the clamp valve to clamp the conduit 17 a clamping action substantially as shown in FIG. 2 is achieved between at least one edge 21 of the aperture 15 and at least one edge of one of the apertures in the hollow member 2, preferably the aperture 14.

To increase this clamping action the edge 21 is preferably provided on a rib 22 for example substantially of triangular cross section such as a right angled triangle substantially as shown for example in the drawings in FIGS. 1 and 2.

The hollow member is preferably provided with a flat, such as at surface 23 and the slide 8 is preferably provided with a corresponding flat 24, so that in use rotation of the slide 8 with respect to the hollow member 2 is substantially prevented.

The use of the invention is as follows.

In use the clamp valve is preferably provided in the open position substantially as shown in FIG. 1 with a pin 20 through the aligned apertures 18 and 19. A conduit 17 having a pliable resilient wall can then be passed therethrough the conduit 17 being positioned for example between a fluid pack 25 and a humidifier device 26.

Once the conduit 17 has been passed through the apertures 13, 14 and 15 the pin 20 is removed and the spring 12 forces the slide 8 to the position substantially shown in FIG. 2 in which the conduit 17 becomes clamped to substantially close the conduit 17 to fluid flow.

If it is desired to open the conduit the button 9 is pressed relative to the body 2 and this can be achieved for example by placing the fingers of the user about the flange 5 and pushing against the button 9 with the thumb, or otherwise as desired.

Thus it can be seen that a clamp valve is provided which at least in the preferred form of the invention provides a pinched tube liquid "on/off" valve that is normally in the "off" position or has a dead-man characteristic. That is to say the clamp valve will return to the off position when an operators hand is removed from the clamp valve.

At least the preferred form of the present invention has the advantage that a reliable cut-off is provided without substantial damage to the conduit being clamped. The clamp valve can be opened by hand pressure and the construction allows low cost part and tool manufacture to be effected. The storage condition, that is to say normally open when a pin is inserted in the further apertures substantially prevents permanent conduit or tube welding before use.

What is claimed is:

1. A clamp valve comprising a hollow member open at one end and having a side wall with a pair of apertures therethrough, a slide movable in said hollow member and having a transverse aperture therethrough so that a conduit having a pliable resilient wall can in use be passed through both said apertures in said wall of said hollow member and through said aperture through said slide, said aperture through said slide having an outer edge *shaped to provide a rib extending inwardly of said aperture and* juxtaposed to an inner edge of one of the apertures in said wall for clamping said conduit between said edges, and biasing means to bias said slide relative to said hollow member to a position for clamping said conduit between said edges so that said conduit is normally closed to fluid flow.

[2. A clamp valve as claimed in claim 1 wherein said edge of said aperture through in said slide is shaped to provide a rib extending inwardly of said aperture.]

3. A clamp valve as claimed in claim [2] *1* wherein said rib is substantially triangular in cross section.

4. A clamp valve as claimed in claim 1 wherein said biasing means comprise a compression spring between the end of said slide and a closed end of said hollow member opposite the one end.

5. A clamp valve as claimed in claim 1 wherein further apertures are provided in said hollow member and said slide arranged so that a pin or the like can be positioned through said further apertures when aligned to retain said clamp in a substantially open position.

6. A clamp valve as claimed in claim 1 wherein said hollow member and said slide each have a flat thereon to substantially prevent relative rotation between said hollow member and said slide.

* * * * *